US00PP19664P2

(12) United States Plant Patent
Silva

(10) Patent No.: US PP19,664 P2
(45) Date of Patent: Jan. 27, 2009

(54) ***STYRAX* PLANT NAMED 'FRAGRANT FOUNTAIN'**

(50) Latin Name: *Styrax japonicus*
Varietal Denomination: Fragrant Fountain

(76) Inventor: Crispin Silva, 31997 S. One Way Mollala, Molalla, OR (US) 97036

( * ) Notice: Subject to any disclaimer, the term of this patent is extended or adjusted under 35 U.S.C. 154(b) by 0 days.

(21) Appl. No.: 12/069,392

(22) Filed: Feb. 11, 2008

(51) Int. Cl.
*A01H 5/00* (2006.01)

(52) U.S. Cl. ..... Plt./216

(58) Field of Classification Search ..... Plt./216
See application file for complete search history.

*Primary Examiner*—Annette H Para
*Assistant Examiner*—S. B McCormick Ewoldt

(57) ABSTRACT

A new cultivar of *Styrax* plant named 'FRAGRANT FOUNTAIN' that is characterized by a weeping habit, profuse blooms which are strongly scented, and rapid growth. In combination these traits set 'FRAGRANT FOUNTAIN' apart from all other existing varieties of *Styrax* known to the inventor.

7 Drawing Sheets

Genus: STYRAX
Species: *japonicus.*
Denomination: 'FRAGRANT FOUNTAIN'.

BACKGROUND OF THE INVENTION

The present invention relates to a new and distinct cultivar of Styrax or Weeping Japanese Snowbell that is grown for use as a small tree. It is known botanically as *Styrax japonicus* and will be referred to hereinafter by the cultivar name 'FRAGRANT FOUNTAIN'.

'FRAGRANT FOUNTAIN' is the product of a breeding program started by the inventor in a cultivated area of Mollala, Oreg. The primary focus of the breeding program is to produce new cultivars of shrubs and trees with attractive foliage.

Seed was collected from *Styrax japonicus* 'Rosea' (unpatented), which is the female parent, in 1994 and germinated in 1996. From this batch of seedlings, 'Fragrant Fountain' was selected. As 'Fragrant Fountain' possesses a weeping habit, the inventor considers that the male parent was *Styrax japonicus* 'Carillon' (unpatented), another cultivar which possesses a weeping habit and was being grown by the inventor at the time the seed was collected.

'FRAGRANT FOUNTAIN' exhibits a strongly weeping form, very pronounced fragrance, and is faster growing than other cultivars known to the inventor, including the parent plants 'Rosea' and 'Carillon'.

Asexual reproduction of the new cultivar was first accomplished by the inventor in 2000 in a cultivated area of Molalla, Oreg. The method of asexual propagation used was softwood cuttings. Since that time the characteristics of the new cultivar have been determined stable and are reproduced true to type in successive generations of asexual propagation.

SUMMARY OF THE INVENTION

The following traits have been repeatedly observed and represent the characteristics of the new *Styrax cultivar* 'FRAGRANT FOUNTAIN'. These traits in combination distinguish 'FRAGRANT FOUNTAIN' from all other varieties of *Styrax* known to the inventor. 'FRAGRANT FOUNTAIN' has not been tested under all possible conditions and phenotypic differences may be observed with variations in environmental, climatic and cultural conditions, without however any change in genotype.

1. *Styrax* 'FRAGRANT FOUNTAIN' exhibits a strongly weeping form.
2. *Styrax* 'FRAGRANT FOUNTAIN' flowers emit a pronounced pleasant fragrance.
3. *Styrax* 'FRAGRANT FOUNTAIN' is 2.7 m tall by 1.5 m wide at 8 years.
4. *Styrax* 'FRAGRANT FOUNTAIN' blooms in late spring.
5. *Styrax* 'FRAGRANT FOUNTAIN' is hardy to USDA Hardiness Zone 6.

BRIEF DESCRIPTION OF THE DRAWINGS

The accompanying color drawings illustrate the overall appearance of the new *Styrax* variety 'FRAGRANT FOUNTAIN' showing colors as true as it is reasonably possible to obtain in colored reproductions of this type. Colors in the drawings may differ from the color values cited in the detailed botanical description, which accurately describe the actual colors of the new variety 'FRAGRANT FOUNTAIN'.

Figure 1:
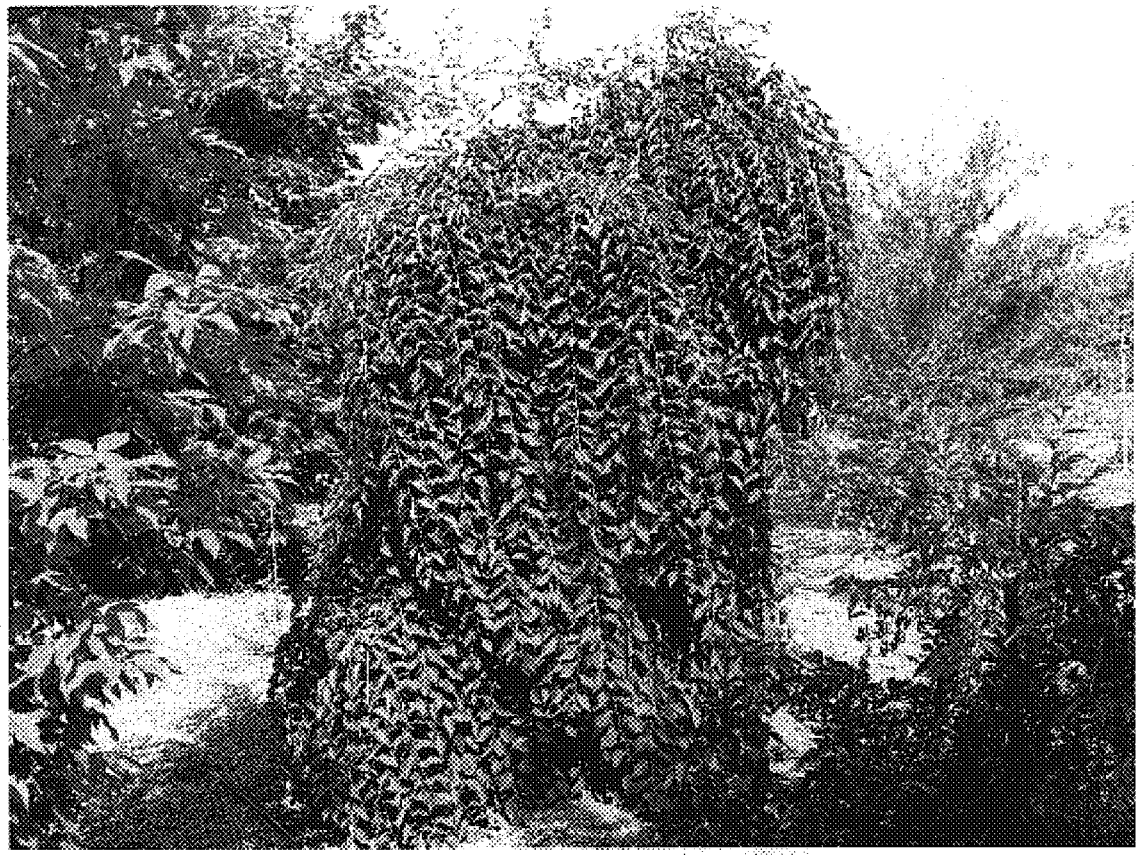
FIG. 1 shows the original tree at approximately 8 years of age.
Figure 2:
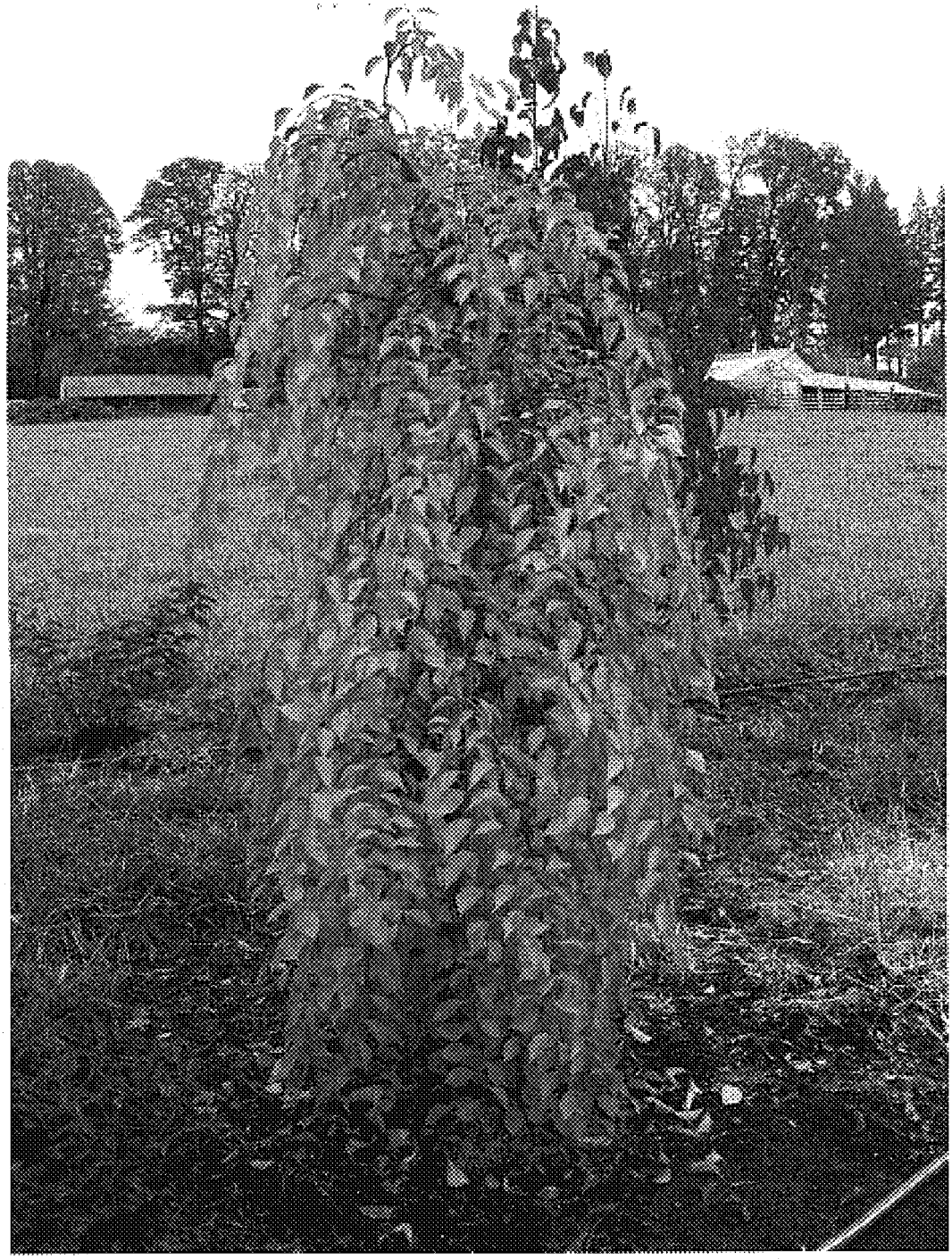
FIG. 2 shows the fall color of the foliage in a tree that is approximately 6 years of age.
Figure 3:
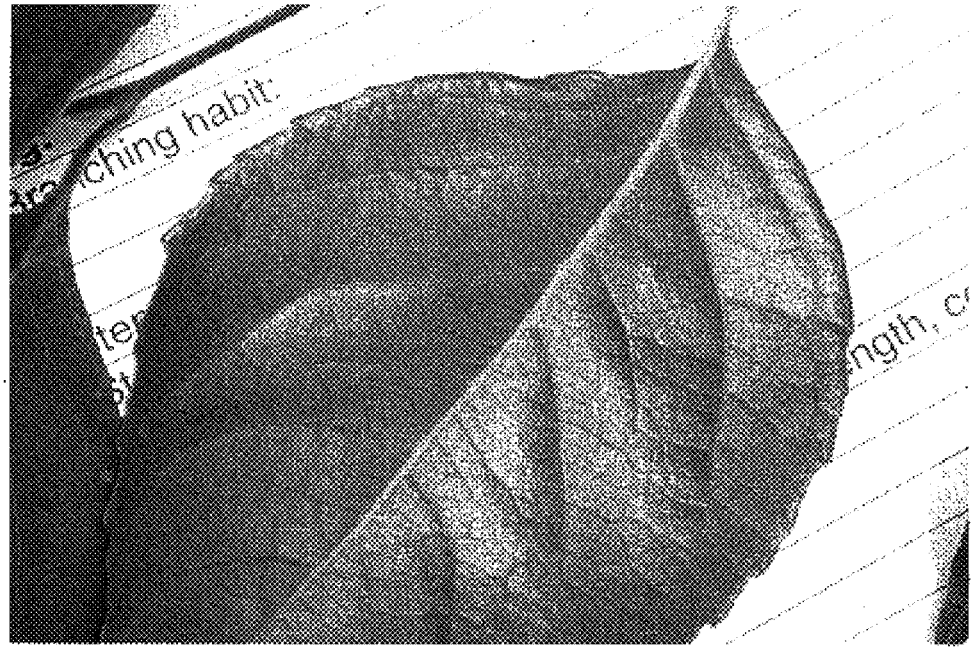
FIG. 3 shows a close up view of the under side of a leaf of 'FRAGRANT FOUNTAIN'
Figure 4:
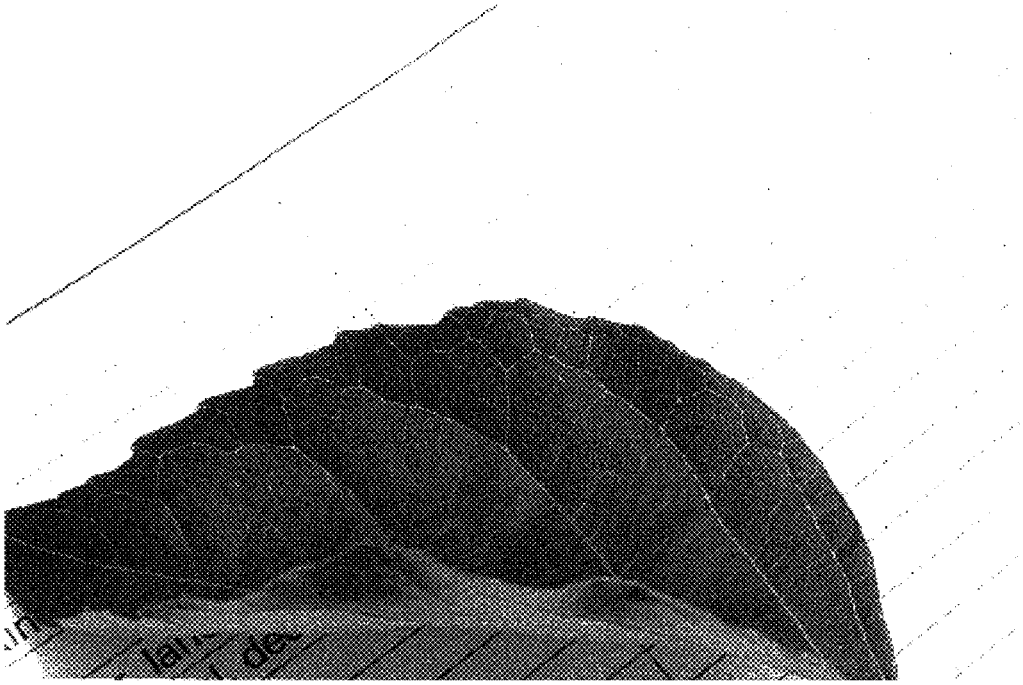
FIG. 4 shows the margins of a leaf of 'FRAGRANT FOUNTAIN'
Figure 5:
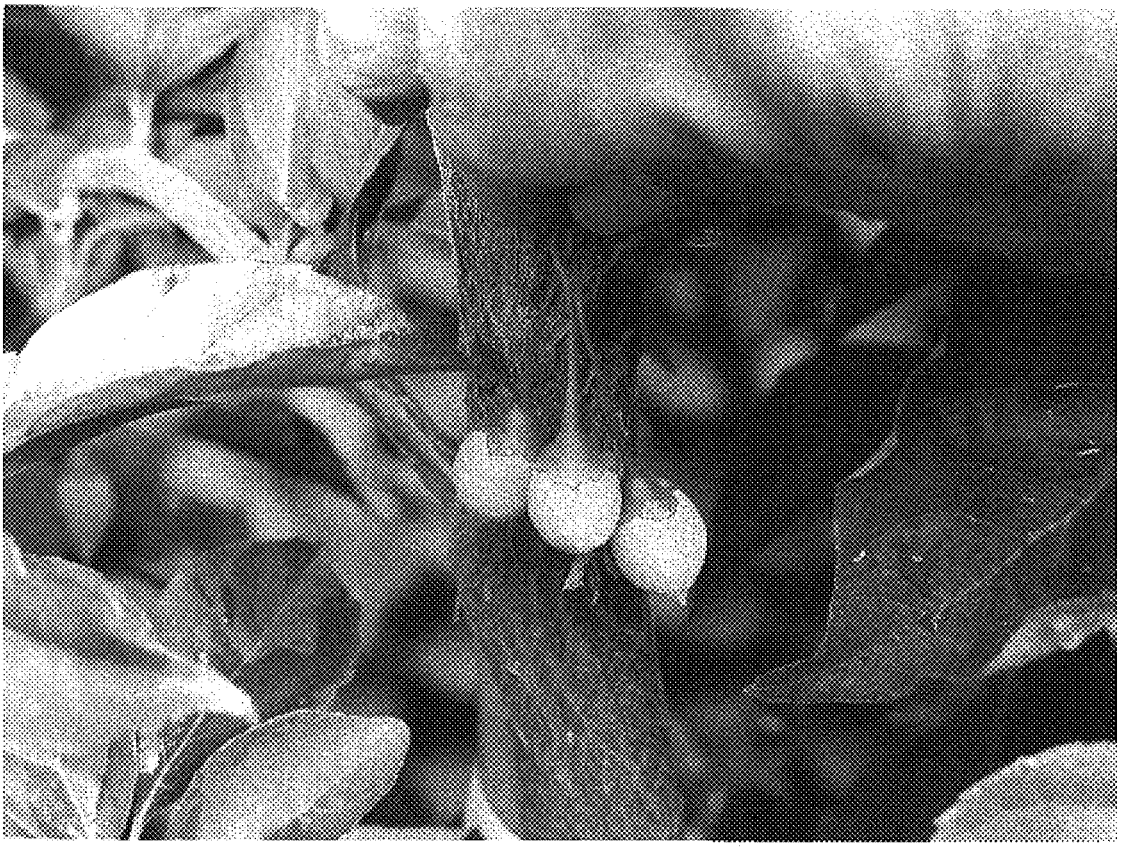
FIG. 5 shows the fruits and bark of 'FRAGRANT FOUNTAIN'
Figure 6:
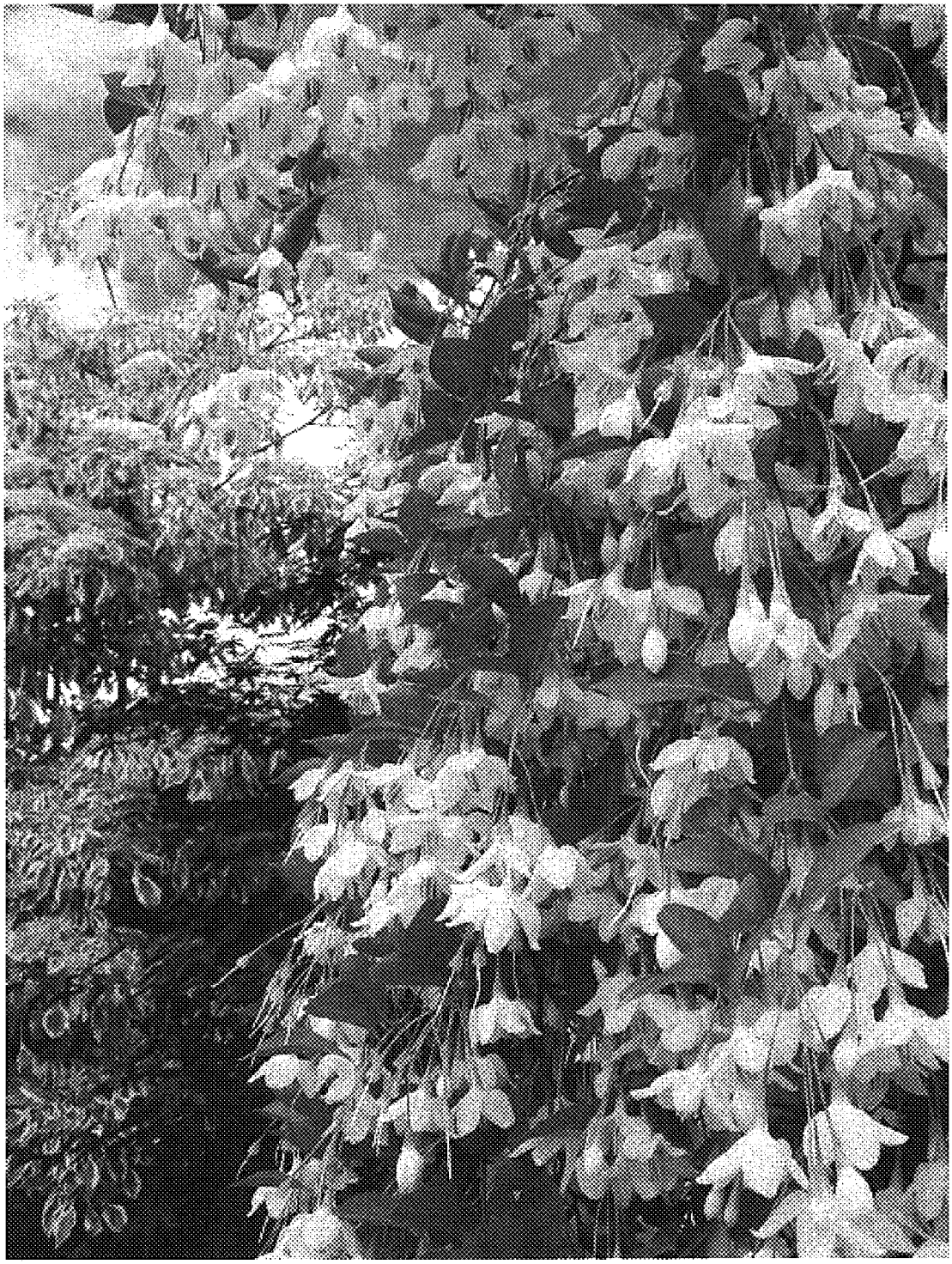
FIG. 6 shows the prolific flower set of 'FRAGRANT FOUNTAIN'
Figure 7:
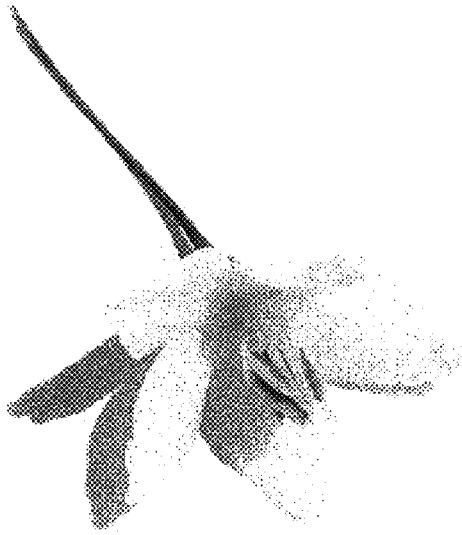
FIG. 7 and FIG. 8 show the flower of 'FRAGRANT FOUNTAIN'
Figure 8:
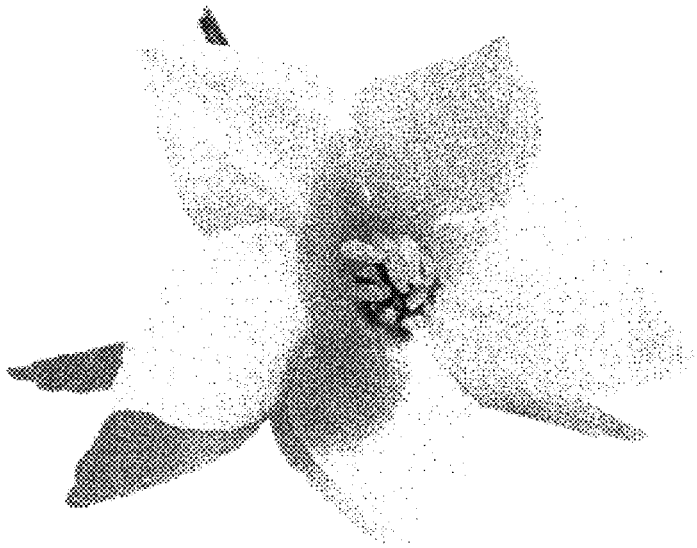
Figure 9:
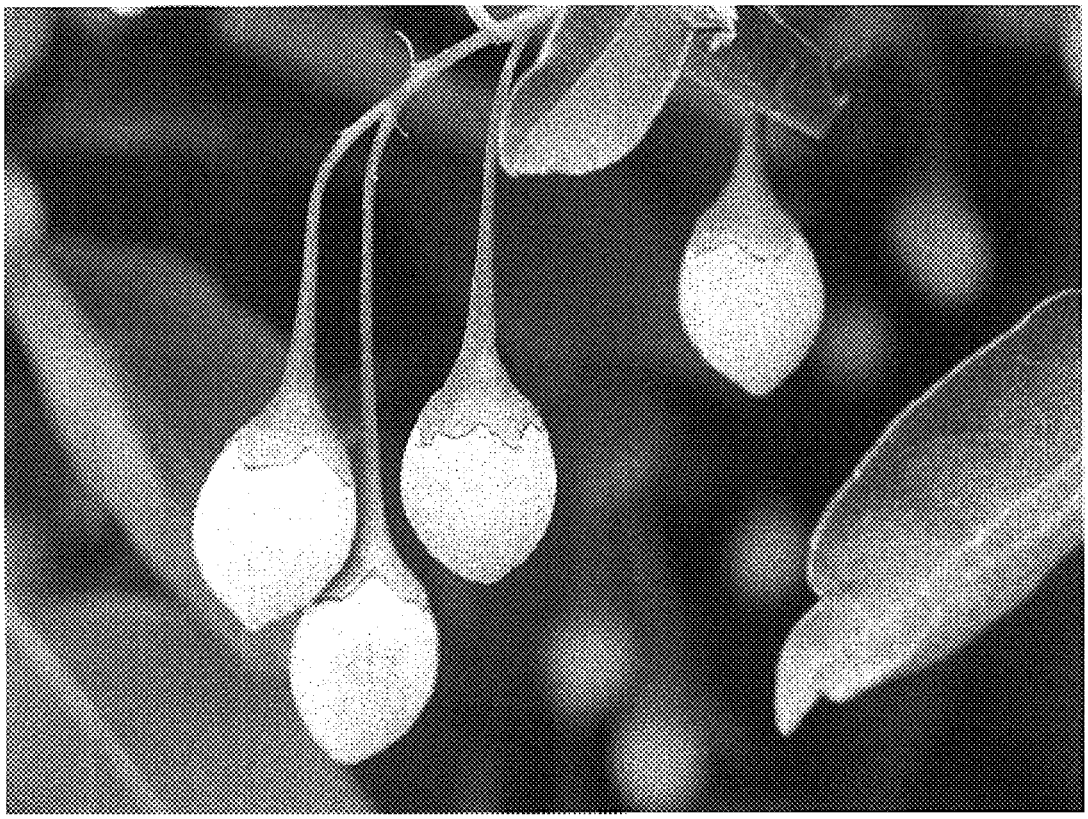
FIG. 9 shows a close-up of the fruits of 'FRAGRANT FOUNTAIN'

All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'FRAGRANT FOUNTAIN'. Data was collected from 4 years-old plants grown in out of doors in Mollala, Oreg. The color determinations are in accordance with the 1966 edition of The Royal Horticultural Society Color Chart of The Royal Horticultural Society, London, England, except where general color terms of ordinary dictionary significance are used. No chemicals were used to treat the plants. Growing conditions are typical to other *Styrax*.

Botanical classification: *Styrax*.
Species: *japonicus*.
Common name: Japanese Snowbell.
Commercial classification: Deciduous flowering tree.
Use: Landscape plant.
Parentage: *Styrax japonicum* 'Rosea' (female parent)×*Styrax japonicum* 'Carillon' (male parent).
Plant description:
- *Plant habit.*—Weeping.
- *Plant dimensions* (1 *year*).—45 cm in height; 25 cm in width.
- *Plant dimensions* (8 *years old*).—2.7 m in height; 1.5 m in width.
- *Plant hardiness.*—USDA Zone 6–9.
- *Type.*—Deciduous flowering tree.
- *Propagation.*—Grafting, budding, or with semi-hardwood cuttings.
- *Growth rate.*—Vigorous — faster than other cultivars in the species.
- *Cultural requirements.*—Moist soil with good drainage.
- *Diseases and pests.*—None known to the inventor.

Stem:
- *Color.*—177A on the upper, sun-exposed portion of the branch; 138B on the under, shaded portion of the branch.
- *Shape.*—Rounded.
- *Dimensions.*—On current year's growth, at 10 cm from the ground, the diameter is 2.5 cm.
- *Internode length.*—An average of 3 cm.
- *Surface.*—Covered with tiny hairs.

Foliage:
- *Arrangement.*—Alternate.
- *Leaves.*—Division: Simple. Shape: Obovate to ovate. Dimensions: Approximately 7 cm in length and 4.5 cm in width. Apex: Acuminate. Base: Acute. Venation pattern: Reticulate. Vein color (adaxial): 145A. Vein color (abaxial): 144D. Margin type: Serrate. Surface texture: Slightly rough. Mature leaf color (adaxial): 147A. Mature leaf color (abaxial): 137B. Young leaf color (both surfaces): 137A. Attachment: Petiolate
- *Petiole.*—Dimensions: 10 mm in length and 1.5 mm in diameter. Surface: Rough. Color: 144A.

Inflorescence:
- *Form.*—Raceme.
- *Arrangement.*—Terminal.
- *Quantity of flowers per inflorescence.*—3 to 5.
- *Flower period.*—May or June; flowering duration approximately 2 weeks.
- *Flower.*—Diameter of flower (including calyx, corolla, petals): 2 cm. Height of flower: 1.5 cm. Bud shape: Oval Bud color: Whitish, closest to 155D. Bud surface: Smooth Bud dimensions: 6 mm in length and 4 mm in diameter. Corolla dimensions: Approximately 2 cm in length and 3.5 cm in width. Corolla surface: Glabrous. Corolla tube color: Whitish, closest to 155D. Number of petals: 5 Petals fused or unfused: Unfused. Petal shape: Ovate. Petal color (both surfaces): Closest to 155D, but whiter. Petal surfaces (both): Smooth. Peduncle dimensions: 1 cm to 1.5 cm in length and 0.5 mm to 1 mm in width. Peduncle shape: Campanulate. Peduncle color: 144B at base. Peduncle surface: Minute whitish hairs.

Reproductive organs:
- *Pistil.*—1 in number.
- *Pistil dimensions.*—8 mm long.
- *Pistil color.*—White.
- *Pistil surface.*—Smooth.
- *Stigma shape.*—Rounded.
- *Stigma dimensions.*—Approximately 0.5 mm in length and 0.75 mm in width.
- *Stigma color.*—White.
- *Style shape.*—Linear.
- *Style dimensions.*—Approximately 1 cm in length and 1.5 mm in width.
- *Style color.*—White.
- *Number of stamens.*—10.
- *Stamens fused or unfused at base.*—Unfused.
- *Stamen dimensions.*—8 mm in length and 1 mm in width.
- *Stamen color.*—White.
- *Anther shape.*—Linear.
- *Anther dimensions.*—5 mm in length and 1 mm in width.
- *Anther color.*—White.
- *Pollen color.*—Yellow.
- *Pollen amount.*—Not applicable.
- *Ovary position.*—Superior.
- *Ovary shape.*—Rounded.
- *Ovary dimensions.*—3 mm in length and 2 mm in width.

*Ovary color.*—White.

Seed:
- *Shape of fruit.*—Ovoid.
- *Fruit dimensions.*—Approximately 1 cm by 1.2 cm.
- *Fruit color.*—157B.
- *Quantity of seeds per capsule.*—2.
- *Seed shape.*—Ovoid.
- *Dimension of seed.*—Approximately 1.2 cm in length and 1.0 cm in width.
- *Color.*—166C.

What is claimed is:

1. A new and distinct cultivar of *Styrax* plant named 'FRAGRANT FOUNTAIN' as described and illustrated herein.

* * * * *